United States Patent [19]

Anton et al.

[11] Patent Number: 5,859,126
[45] Date of Patent: Jan. 12, 1999

[54] COATINGS CONTAINING FLUORINATED ESTERS

[75] Inventors: Douglas Robert Anton; Jack Robert Kirchner, both of Wilmington, Del.; William Wesley Bennett, Jr., Carney's Point, N.J.

[73] Assignee: E. I. du Pont de Nemours and Company, Wilmington, Del.

[21] Appl. No.: 704,487

[22] Filed: Aug. 7, 1996

Related U.S. Application Data

[63] Continuation-in-part of Ser. No. 529,899, Sep. 18, 1995, Pat. No. 5,637,657.

[51] Int. Cl.$^6$ ............................. C08L 75/04; C08L 67/07; C08L 67/08; C08F 283/00
[52] U.S. Cl. ................................ 525/7; 525/32.1; 525/44; 525/48; 525/445; 525/454; 525/455; 524/282; 524/307; 524/316
[58] Field of Search ..................................... 524/307, 316, 524/282; 525/7, 32.1, 44, 48, 445, 454, 455

[56] References Cited

U.S. PATENT DOCUMENTS

| | | | |
|---|---|---|---|
| 3,378,609 | 4/1968 | Fasick et al. | 260/890 |
| 3,462,296 | 8/1969 | Raynolds et al. | 117/161 |
| 3,491,169 | 1/1970 | Raynolds et al. | 260/900 |
| 3,923,715 | 12/1975 | Dettre et al. | 260/29.6 |
| 4,054,592 | 10/1977 | Dear et al. | 560/25 |
| 4,097,642 | 6/1978 | Dear et al. | 428/262 |
| 4,401,780 | 8/1983 | Steel | 524/225 |
| 4,539,006 | 9/1985 | Langford | 8/94.1 |
| 4,595,518 | 6/1986 | Raynolds et al. | 252/8.6 |
| 4,735,848 | 4/1988 | Kondo et al. | 428/219 |
| 4,758,471 | 7/1988 | Arioka et al. | 428/336 |
| 4,946,992 | 8/1990 | Falk et al. | 560/227 |
| 4,958,039 | 9/1990 | Pechhold | 556/421 |
| 5,087,672 | 2/1992 | Babirad et al. | 525/329.5 |
| 5,188,747 | 2/1993 | Kai et al. | 252/54 |
| 5,350,878 | 9/1994 | Caporiccio | 560/227 |
| 5,637,657 | 6/1997 | Anton | 525/445 |
| 5,670,573 | 9/1997 | Kirchner | 525/48 |

FOREIGN PATENT DOCUMENTS

| | | |
|---|---|---|
| 0 068 040 | 1/1983 | European Pat. Off. . |
| 614874-A2 | 9/1994 | European Pat. Off. . |
| 694 532 | 1/1996 | European Pat. Off. . |
| 28 21 495 | 11/1979 | Germany . |
| 50-047t912 | 4/1975 | Japan . |
| 222272 | 12/1984 | Japan . |
| 3-167158 | 7/1991 | Japan . |
| 05232718A | 9/1993 | Japan . |
| 05246951A | 9/1993 | Japan . |
| 026204 | 1/1995 | Japan . |
| WO 91/18859 | 12/1991 | WIPO . |

OTHER PUBLICATIONS

Database WPI, Week 9514, Derwent Publications Ltd., London, GB; AN 95–102116, XP002022182 & JP 07 026 204 A (Nippon Polyurethane Kogyo KK), Jan. 27, 1995 (Abstract).

Paul "Surface Coatings Science and Technology" pp. 276–279.

*Primary Examiner*—David Buttner

[57] ABSTRACT

Coating compositions containing an alkyd, urethane or unsaturated polyester resin, and an ester of an unsaturated acid and a fluorinated alcohol wherein the cured coating has an advancing hexadecane contact angle of at least about 40 degrees and durable improved oil and water repellency is disclosed.

8 Claims, No Drawings

COATINGS CONTAINING FLUORINATED ESTERS

CROSS REFERENCE TO RELATED APPLICATION

This application is a continuation-in-part of U.S. Ser. No. 08/529,899 filed Sep. 18, 1995 now U.S. Pat. No. 5,673,657.

FIELD OF THE INVENTION

This invention relates to coating compositions containing fluorinated esters of unsaturated carboxylic acids that provide durable oil- and water-repellent surfaces to the cured coating, and the cured coatings derived from such compositions.

BACKGROUND OF THE INVENTION

The coating compositions of interest in the present invention are alkyd coating compositions, Type I urethane coating compositions, and unsaturated polyester resin coating compositions, typically a paint, clear coating, or stain. All the above-listed coating compositions after drying or curing show low hexadecane contact angles, are readily wetted by oil, and are susceptible to soiling. The coating compositions are described in Outlines of Paint Technology, Halstead Press, New York N.Y., Third edition, 1990) and Surface Coatings Vol. I, Raw Materials and Their Usage (Chapman and Hall, New York N.Y., Second Edition, 1984). A common factor in these coating compositions is an unsaturated resin or prepolymer structure that permits the polymerization of olefinic groups in the backbone or sidechain.

Conventional alkyd coatings utilize, as the binder or film-forming component, a curing or drying alkyd resin. Alkyd resin coating compositions contain unsaturated aliphatic acid residues derived from the drying oils. These resins spontaneously polymerize in the presence of oxygen or air to yield a solid protective film. The polymerization is termed "drying" or "curing" and occurs as a result of autoxidation of the unsaturated carbon-carbon bonds in the aliphatic acid component of the oil by atmospheric oxygen. When applied to a surface as a thin liquid layer of formulated alkyd coating, the cured films that form are relatively hard, non-melting, and substantially insoluble in many organic solvents that act as solvents or thinners for the unoxidized alkyd resin or drying oil. Such drying oils have been used as raw materials for oil-based coatings and are described in the literature.

Urethane coatings are classified by ASTM D-1 into five categories. Type I urethane coatings contain a pre-reacted autoxidizable binder as described in Surface Coatings Vol. I, previously cited. Type I urethane binders, also termed urethane oils, oil-modified polyurethanes, or urethane alkyds, are the largest volume category of polyurethane coatings, and include typical paints, clear coatings, or stains. Urethane coatings typically contain the reaction product of a polyisocyanate, usually toluene diisocyanate, and a polyhydric alcohol ester of drying oil acids. The cured coating is formed by air oxidation and polymerization of the unsaturated drying oil residue in the binder.

Unsaturated polyester resins contain as the unsaturated prepolymer the product obtained from the condensation polymerization of a glycol such as 1,2-propylene glycol or 1,3-butylene glycol with an unsaturated acid such as maleic (or of maleic and a saturated acid, e.g., phthalic) in the form of anhydrides. The unsaturated prepolymer is a linear polymer containing unsaturation in the chain. This is dissolved in a suitable monomer, for instance styrene, to produce the final resin. The film is produced by copolymerization of the linear polymer and monomer by means of a free radical mechanism. The free radicals can be generated by heat, or more usually by addition of a peroxide, such as benzoyl peroxide, separately packaged and added before use. Such coating compositions are frequently termed "gel coat" finishes. In order that curing can take place at room temperature the decomposition of peroxides into free radicals is catalyzed by certain metal ions, usually cobalt. The solutions of peroxide and cobalt compound are added separately to the mix and well stirred before application. The unsaturated polyester resins that cure by a free radical mechanism are also suited to irradiation curing, using, for instance, ultraviolet light. This form of cure, in which no heat is produced, is particularly suited to films on wood or board. Other radiation sources, for instance electron-beam curing, are also used.

Certain fluorinated materials are known to provide oil repellency to substrates such as textiles and carpets. For instance, perfluoroalkyl iodides have been converted sequentially to perfluoroalkyl ethyl iodides, to perfluoroalkyl ethyl alcohols, to monomers and finally polymers for application to such substrates.

The use of fluoroalkyl alcohol esters of alkanoic acids generally as lubricating aids is known. For instance, the perfluoroalkyl ethyl ester of stearic acid (octadecanoic acid) has been used for imparting lubricity and repellency to various plastics. Also, Nishihara et al., JP308469 (1989) disclose the preparation of aliphatic carboxylic acid esters of various fluorinated alcohols in general as lubricants and their use as lubricants for ferromagnetic metal thin film-type magnetic recording media.

Adding perfluoroalkyl ethyl stearate, a noncuring ("non-drying") fluoroalkyl ethanol ester of a saturated vegetable oil, for instance, to alkyd, urethane, or unsaturated polyester coatings in suitable formulations, however, does not provide durable oil and water repellency. Since the fluorinated component is saturated, it is not chemically bound with the cured polymer. Thus the oil repellency is not durable and is readily lost when the surface is washed or otherwise cleaned. By durable oil repellency and durable increased hexadecane contact angles are meant that the surface properties of the cured coatings are retained following surface cleaning.

Certain perfluoroalkyl ethyl esters that do not react with enamel binders have been listed by Deibig et al. in German patent DE 28 21 495 C2 and include bis (perfluorohexylethyl) maleate. Bis(perfluoroalkylethyl) maleate esters behave similarly to the stearyl esters and do not show durable oil repellency after scrubbing. Presumably the double bond in the ester is sufficiently deactivated by two immediately adjacent fluoroalcohol ester groups and is not sufficiently incorporated into the binder to provide durable oil repellency.

It is highly desirable to be able to provide cost effective and wash resistant oil repellency to alkyd coatings, Type I urethane coatings, and unsaturated polyester coatings. The present invention provides such compositions.

SUMMARY OF THE INVENTION

The present invention comprises a coating composition comprising

A. an ester of an unsaturated acid and a fluorinated alcohol or thiol selected from the group consisting of the Formula 1a, 1b, and 2 as follows:

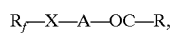

$R_f$—X—A—OC—R,             Formula 1a

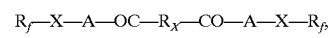
$$R_f-X-A-OC-R_x-CO-A-X-R_f,\qquad\text{Formula 1b}$$

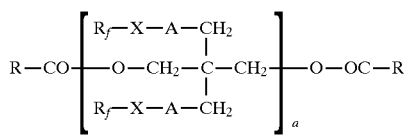
$$\text{Formula 2}$$

wherein:
- $R_f$ is a $C_2$–$C_{20}$ perfluoroalkyl radical, or a $C_5$–$C_{38}$ perfluoroalkyl radical having at least one ether oxygen atom;
- R is a $C_3$–$C_{21}$ unsaturated aliphatic hydrocarbon radical, a $C_8$–$C_{13}$ aryl radical having at least one non-aromatic double bond, or mixtures thereof;
- X is independently —$(CH_2)_m$-, —$CON(R_1)R_2$-, —$SO_2N(R_1)R_2$- or —$(OCH_2CHR_3)_bO$-, wherein m is 1 to about 20; b is 3 to about 15;
- $R_1$ is H or alkyl radical of 1 to about 4 carbon atoms, $R_2$ is $C_1$–$C_{12}$ alkylene, and $R_3$ is H or $CH_2Cl$;
- A is C or S;
- $R_x$ is a divalent $C_3$–$C_{22}$ unsaturated aliphatic hydrocarbon radical; a divalent $C_8$–$C_{13}$ aryl radical having at least one non-aromatic double bond, or mixtures thereof;
- a is 1 or 2;

and

B. an alkyd, urethane or unsaturated polyester resin; wherein a cured coating resulting from said coating composition has an advancing hexadecane contact angle of at least about 40 degrees.

The present invention further comprises the coating compositions defined above in a dry or cured state.

The present invention further comprises a method of improving the oil repellency and water repellency of an alkyl, urethane or unsaturated polyester coating composition comprising adding to said coating composition an ester as defined above.

The present invention further comprises a perfluoroalkyl alkenoate ester having the structure

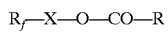
$$R_f-X-O-CO-R$$

wherein
- O—CO—R is a $C_{10}$–$C_{24}$ alkenoic acid residue containing at least two double bonds;
- X is a divalent radical containing 1–20 atoms in the chain; and
- $R_f$ is a $C_1$–$C_{20}$ perfluoroalkyl group; and $R_f$—X is selected from the group consisting of
  - $R_f$—$SO_2N(Et)$—$CH_2CH_2$—
  - $R_f$—$SO_2N(Me)$—$CH_2CH_2$—
  - $R_f$—$SO_2N(Bu)$—$CH_2CH_2$—.

DETAILED DESCRIPTION OF THE INVENTION

This invention comprises coating compositions containing an alkyd, urethane or unsaturated polyester resin and an ester of an unsaturated acid and a fluorinated alcohol or thiol wherein a cured coating resulting from said coating composition has an advancing hexadecane contact angle of at least about 40 degrees.

By the term "alkyd coating", as used hereinafter, is meant a conventional liquid coating based on alkyd resins, which contain unsaturated aliphatic acid residues derived from drying oils, wherein said resins spontaneously polymerize in the presence of oxygen or air to yield a solid protective coating as a result of autoxidation of the unsaturated bonds by atmospheric oxygen. Included are acrylic alkyd resins wherein an acrylic polymer has been reacted with drying oil fatty acids. The coatings typically include a paint, clear coating, or stain. The alkyd resins are complex branched and cross-linked polyesters.

By the term "urethane coating", as used hereinafter, is meant a conventional liquid coating based on Type I urethane resins containing a prereacted autoxidizable binder, typically a paint, clear coating, or stain. Urethane coatings typically contain the reaction product of a polyisocyanate, usually toluene diisocyanate, and a polyhydric alcohol ester of drying oil acids. The cured coating is formed by air oxidation and polymerization of the unsaturated drying oil residue in the binder.

By the term "unsaturated polyester coating", as used hereinafter, is meant a conventional liquid coating based on unsaturated polyester resins, dissolved in monomers and containing initiators and catalysts as needed, typically as a paint, clear coating, or gel coat formulation. The resin contains as the unsaturated prepolymer the product obtained from the condensation polymerization of a glycol with an unsaturated acid in the form of anhydrides. The prepolymer is a linear polymer containing unsaturation in the chain and is dissolved in a suitable monomer to produce the resin. A cured coating is produced by copolymerization of the linear polymer and monomer by means of a free radical mechanism.

By the term "coating composition", as used herein, is meant a liquid formulation of alkyd, Type I urethane resin, or unsaturated polyester resin, as applied to a substrate. Included are paints, varnishes, finishes, enamels, stains and similar materials.

By the term "cured coating" as used herein is meant the final decorative and/or protective film obtained after the volatile components of a coating composition have evaporated and the polymerizations associated with the curing process are substantially completed.

The ester of an unsaturated acid and a fluorinated alcohol or thiol used in the coating compositions, cured coating compositions, and method of this invention has the Formula 1a, 1b, or 2 as previously defined.

More particularly, in Formulae 1a, 1b, and 2, $R_f$ is selected from the group consisting of (a), (b), and (c) as follows:

(a) $F(CF_2)_n$— wherein n is 2 to about 20;

(b)

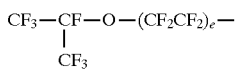
$$CF_3-CF-O-(CF_2CF_2)_e-\\|\\CF_3$$

wherein e is 1 to about 5; and (c)

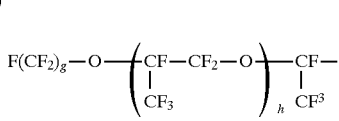

wherein g is 1 to about 6, and h is about 3 to about 10.

Preferred examples of $R_f$—X— include the following: from definition (a) of $R_f$:

1) $F(CF_2)_n(CH_2)_m$– wherein n is 2 to about 20 and m is 1 to about 20;

2) $F(CF_2)_n$—$CON(R_1)R_2$- wherein n, $R_1$ and $R_2$ are as previously defined;

3) $F(CF_2)_n-SO_2(R_1)R_2-$ wherein n, $R_1$ and $R_2$ are as previously defined;
4) $F(CF_2)_n-(OCH_2CHR_3)_dO-$ wherein n, $R_3$ and d are as previously defined; and from definition (b) of $R_f$:

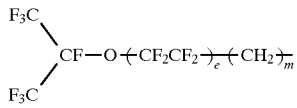

wherein e and m are as previously defined; and
from definition (c) of $R_f$:

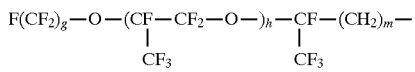

wherein g, h and m are as previously defined.

The esters of unsaturated carboxylic acids and fluorinated alcohols and thiols are useful as components of the coating compositions of the present invention. The coating compositions of the present invention are useful for providing a protective and/or decorative coating to a wide variety of substrates. Such substrates include primarily construction materials and hard surfaces such as wood, metal, wallboard, masonry, concrete, fiberboard, paper and other materials. Upon application, such coating compositions cure by conventional methods, and the cured coatings of the present invention exhibit several valuable properties. Specifically, the cured coatings of this invention, compared with the conventional cured coatings, exhibit improved anti-blocking properties, and improved oil and water repellency and durability thereof, as demonstrated by contact angle measurements. The improved oil and water repellency results in improved soil resistance and cleanability of the surface of the cured coating. The unsaturated fluorinated esters migrate preferentially to the surface of the coating of the present invention, and, by reason of their unsaturation, become chemically bound to the cured resin of the coating, the latter property providing durability to the improved oil and water repellency. By durable oil repellency and durable increased hexadecane contact angles are meant that the advantageous surface properties of the cured coatings of the present invention are retained following various simulations of surface cleaning. Thus the oil and water repellency and cleanability are retained after conventional washing of the surface.

The coating compositions of this invention contain a mixture of an alkyd, Type I urethane, or unsaturated polyester resin and sufficient fluorinated esters of unsaturated carboxylic acids of the above structures such that the coating composition contains 50–10,000 $\mu g/g$ by weight of fluorine, and preferably 150–5,000 $\mu g/g$ of fluorine, in the nonvolatile content of the composition. The cured coating of this invention resulting from said composition has a durable advancing hexadecane contact angle of not less than 40 degrees and a durable receding hexadecane contact angle of not less than 20 degrees.

The contact angle formed between a surface and a drop of liquid is a measure of the wettability or repellency of the surface to the liquid. A wettable surface has low contact angles close to zero degrees, a repellent surface has higher contact angles. Thus the contact angle formed by an oily liquid such as hexadecane is widely used as a measure of the oil repellency of a surface. In general higher hexadecane contact angles indicate that a surface has greater dirt and soil resistance and repellency, and easier cleanability.

The fluorinated esters of unsaturated carboxylic acids used in the compositions and method of this invention can be prepared by conventional processes for the synthesis of esters. Such processes include direct esterification of unsaturated acids with the fluorinated alcohol (for instance a perfluoroalkyl ethanol) or thiol, or transesterification between the fluorinated alcohol or thiol and esters of the unsaturated acids (for instance the glycerol esters comprising a drying oil or the methyl esters of the drying oil acids). The degree of incorporation of the fluorinated alcohol or thiol may be maximized by using a molar excess of the unsaturated acid during esterification or of the unsaturated ester during transesterification.

The requisite unsaturated acids are commercially available. For instance, the drying oil acids are obtained from natural vegetable oils. The acids are obtained in the free acid form from the oils by saponification or hydrolysis, or in the methyl ester form by methanolysis. The proportion of the various acids in the oils are well known. Other unsaturated acids used in the esterification are readily available commercially.

The fluorinated esters of unsaturated carboxylic acids used in the compositions and method of this invention are made from individual unsaturated acids or mixtures thereof, and individual fluorinated alcohols or mixtures thereof or individual fluorinated thiols or mixtures thereof.

A number of fluorinated alcohols are available commercially, and some are listed below. Several perfluoroalkyl ethanols and derivatives are available as ZONYL Fluorotelomer Intermediates from E. I. du Pont de Nemours and Company, Wilmington Del. "ZONYL" BA contains alpha-fluoro-omega-(2-hydroxyethyl)-poly (difluoromethylene) in the form of a mixture of the components of the homologous series of the formula:

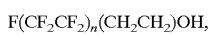

$F(CF_2CF_2)_n(CH_2CH_2)OH,$ wherein the values of n are shown in Table 2 below in the section labeled "Materials".

Other perfluoroalkyl alcohols can also be used in the present invention, such as 2-N-methyl-N-ethanolperfluorooctane sulfonamide, available commercially from Dainippon Ink and Chemicals Inc., DIC Building, 7-20 Nihonbashi 3-chome, Chuo-ku, Tokyo 103, Japan. Fluorinated diols, prepared by the procedure of U.S. Pat. No. 4,946,992 and fluorinated thiols prepared as in U.S. Pat. No. 3,544,663, in particular Example 1 therein, are also suitable.

The fluorinated esters of unsaturated carboxylic acids are incorporated into conventional curable coating compositions in concentrations sufficient to afford a cured coating containing from about 50 to about 10,000 $\mu g/g$ by weight of fluorine and preferably 150 to 5,000 $\mu g/g$ of fluorine based on the nonvolatile content of the coating composition.

The durable hexadecane advancing contact angle of the aired composition is equal to or greater than 40 degrees, preferably equal to or greater than 60 degrees. The durable hexadecane receding contact angle for the cured composition is equal to or greater than 20 degrees, preferably equal to or greater than 40 degrees.

The method of the present invention for improving the oil repellency and water repellency of an alkyd, urethane, or unsaturated polyester coating composition comprises incorporating into such coating compositions the previously described fluorinated esters of an unsaturated carboxylic acid and fluorinated alcohol or thiol. The esters can be added in a molten condition or after dissolution in a compatible solvent. Melting or dissolution provides a method to insure the fluorinated esters are readily and completely mixed in the coating composition. Alternatively, the reaction mixture in which the esters were synthesized may be used, without isolation of the esters, provided any reaction solvents were chosen to be appropriate for the final coating composition and the reaction product is heated to ensure homogeneity. Examples of solvents compatible with the components of the coating compositions of this invention are mineral spirits, deodorized mineral spirits, Stoddard solvent, and other solvents compatible with the specific coating composition and coating.

To prepare coating compositions of the present invention containing an alkyd resin, the fluorinated esters are heated to about 90° C. with stirring until a homogeneous and fully melted mixture is obtained. The hot liquid is poured into the alkyd coating composition and stirred to give a homogeneous mixture. Alternatively, the heated fluorinated esters are dissolved in a suitable solvent compatible with the alkyd coating composition, such as Stoddard solvent, and the solution of fluorinated esters subsequently added to the alkyd coating compositions. The preparation of the coating compositions of the present invention containing Type I urethanes and a fluorinated ester as previously described is accomplished as described above for alkyd-containing coating compositions. The preparation of coating compositions of the present invention containing unsaturated polyesters and the fluorinated ester previously described is accomplished as described above for the alkyd-containing coating compositions, with the addition of the fluorinated esters being made to the alkyd/styrene mix.

Methods of application of the coating compositions to surfaces, and the drying properties of the coating compositions are essentially unaffected by the addition of the fluorinated esters of unsaturated carboxylic acids.

While not wishing to be bound by theory, it is believed that the mechanism of the generation of the advantageous properties of the cured compositions of this invention is via bonding of the fluorinated esters into the coating during curing. It is believed that the fluorinated esters of unsaturated carboxylic acids used in this invention, when applied to a surface as part of a liquid coating composition, migrate to the coating surface before curing, becoming concentrated at the surface, and are chemically bound into the coating during curing, thus providing durable oil and water repellency to the cured coating.

Water repellent surfaces resulting from an oriented fluorocarbon surface, including the surfaces of the coatings of this invention, are frequently subject to reversible "inversion" on prolonged exposure to water or aqueous solutions. The water repellency returns after drying.

TEST METHODS

Method 1—Contact Angle Measurement

Contact angles are measured by the Sessile Drop Method which is described in A. W. Adamson "The Physical Chemistry of Surfaces", Fifth Edition, Wiley & Sons, New York, 1990. Additional information on the equipment and procedure for measuring contact angles is provided by R. H. Dettre et al. in "Wettability", Ed. by J. C. Berg, Marcel Dekker, New York, 1993.

In the Sessile Drop Method, a Ramè-Hart optical bench available from Ramè-Hart Inc., 43 Bloomfield Ave., Mountain Lakes, N.J., is used to hold the substrate in the horizontal position. The contact angle is measured at a prescribed temperature with a telescoping goniometer from the same manufacturer. A drop of test liquid is placed on a surface and the tangent is precisely determined at the point of contact between the drop and the surface. An advancing angle is determined by increasing the size of the drop of liquid and a receding angle is determined by decreasing the size of the drop of liquid. The data are presented typically as advancing and receding contact angles.

The relationship between water and organic liquid contact angles, and cleanability and dirt retention of surfaces is described in A. W. Adamson, above. In general, higher hexadecane contact angles are indicative that a surface has greater dirt and soil resistance and repellency, and easier cleanability of the surface.

By durable oil repellency and durable increased hexadecane contact angles are meant that the advantageous surface properties of modified cured coatings of the present invention are retained following surface cleaning.

The water and hexadecane advancing and receding contact angles of the coating compositions of the present invention were measured on coatings cast on 6.5×17 inch (16.5×43.2 cm) Leneta P-121-10N dull black, scrub test panels available from Leneta Company, Mahwah, N.J. The coating compositions were prepared as described above with the fluoroester added in an amount to give a 1000 $\mu$g/g fluorine concentration in the blended product. The fluoroester containing coating composition was applied to the Leneta test panel using a 7 mil (0.18 mm) film caster. The test panel was anchored to a Gardco DP-1218L Leveling Drawdown Plate (Paul N. Gardner Co., Pompano Beach Fla.) and was cleaned before coating by wiping with isopropyl alcohol wet cheesecloth. The coated panel typically was cured for seven days at ambient room conditions before testing.

Method 2—Detergent Wash Durability

Wash durability of the fluoroester containing coating composition to surface cleaning was determined using a Gardco Model D10 Wash & Wear Tester (Paul N. Gardner Co., Pompano Beach Fla.) and a Gardco WA-2225 abrasion boat. A 6.5×1 inch (16.5×2.5 cm) test strip cut from the coated Leneta test panel was positioned on the test sample tray and fastened thereto with ¾ inch (1.9 cm) wide transparent tape such that about a 2×¾ inch (5.1×1.9 cm) portion of the coated test panel would be scrubbed. The abrasion boat base plate was covered with a folded 9×9 inch (22.9× 22.9 cm) piece of De Royal Textiles Idealfold bleached grade 20B cotton cheesecloth available from DeRoyal Textiles, Camden, S.C. The cheesecloth was folded perpendicular to the seam in half and half again and was fastened to the base plate such that the scrubbing surface layers were seam free. The cheesecloth pad was wet with 20 ml of a 1% aqueous Tide detergent (Proctor and Gamble Co., Cincinnati, Ohio) solution before the test strip was scrubbed. The test strip was removed after 10 scrub cycles, washed free of the Tide solution with water and air dried one day before advancing and receding hexadecane contact angles were measured on the scrubbed surface.

Method 3—Anti-Blocking Test

ASTM 4946-89 provides a method for measuring the anti-blocking (non-stick) properties of surface coatings. The painted surfaces of flat panels are placed face-to-face. A No. 8 stopper is placed atop the pair, and a 1000 g weight is placed atop the stopper, creating a pressure of 1.8 psi (12.4 kPa). The weighted pair is held for 30 minutes at 120°+/−5° F. (49°+/−3° C.), then cooled at room temperature for 30 minutes. Samples are then peeled and tack rating noted. The blocking resistance is assessed according to the Table 1 below:

TABLE 1

ASTM 4946-89 Anti-Blocking Test Ratings

| Blocking Resistance Numerical Ratings | Type of Separation | Performance |
|---|---|---|
| 10 | no tack | perfect |
| 9 | trace tack | excellent |
| 8 | very slight tack | very good |
| 7 | very slght to slight tack, | good to very good |
| 6 | slight tack | good |
| 5 | moderate tack | fair |
| 4 | very tacky; no seal | poor to fair |
| 3 | 5–25% seal | poor |
| 2 | 25–50% seal | poor |
| 1 | 50–75% seal | very Poor |
| 0 | 75–100% seal | very poor |

The general procedure of ASTM 4946-89 was used to measure the anti-blocking properties of the coating compositions of this invention as a function of cure days. The measurements were made using 1.5×1.5 inch (3.8×3.8 cm) sections cut from coated Leneta scrub test panels prepared as described above.

MATERIALS

The following materials were employed in the examples hereinafter unless otherwise indicated.

A. Paints
1) IMPERVO™ White Alkyd High Gloss Enamel, from Benjamin Moore and Company, Montvale, N.J. 07645
2) Enterprise Gloss Polyurethane, from The Valspar Corporation, Wheeling, Ill. 60090
3) SWP Exterior Gloss Oil Base Paint (white), from The Sherwin-Williams Company, Cleveland, Ohio 44101
4) Duron Exterior Alkyd House Paint (white), from Duron, Inc., Bettsville, Md. 20705
5) 75 Neutral Gel Coat, from Fibre Glast Developments Corporation, 1944 Neva Drive, Dayton, Ohio 45414
6) Neste Gel Coat WG30001S, from Neste Polyester Inc., 5106 Wheeler Avenue, Fort Smith, Ark. 72901

B. Fluorinated Alcohols and Thiols
1) ZONYL BA and ZONYL BA-N Fluorotelomer Intermediates of the formula $F(CF_2CF_2)_nCH_2CH_2OH$, from E. I. du Pont de Nemours and Company, Wilmington Del., homologue composition as shown in Table 2

TABLE 2

Homologue Composition for ZONYL BA and ZONYL BA-N

| | Weight Percent Homologue | |
|---|---|---|
| Value of n | ZONYL BA | ZONYL BA-N |
| 3 | 27–37 | 0–3 |
| 4 | 28–32 | 45–52 |
| 5 | 14–20 | 26–32 |
| 6 | 8–13 | 10–14 |
| 7 | 3–6 | 2–5 |
| 8 | 0–2 | 0–2 |
| 9 | 0–1 | 0–1 |

2) FX-42, N-methyl-N-ethanolperfluorooctane sulfonamide, from Dainippon Ink and Chemicals, Inc., DIC Building, 7-20, Nihonbashi 3-chome, Chuo-ku, Tokyo 103, Japan.

3) Bis-(perfluoroalkylethylmercapto)neopentyl glycols of the formula $[F(CF_2CF_2)_nCH_2CH_2SCH_2]_2C(CH_2OH)_2$ where n is 3 to 8, predominantly 3, 4 and 5, prepared by the procedure of U.S. Pat. No. 4,946,992.
4) Perfluoroalkylethyl thiols of the formula $F[CF_2CF_2]_nCH_2CH_2\text{-S-H}$ wherein n is 4 to 7, prepared by the procedure of Example 1 of U.S. Pat. No. 3,544,663.

C. Unsaturated Acids
1) Emery 644 Linseed Fatty Acid, from Henkel Corporation, Emery Group, 11501 Northlake Drive, Cincinnati, Ohio 45249
2) TRLA-50 Linseed Fatty Acid, from Twin Rivers Technologies Inc., 780 Washington Street, Quincy, Mass., 02169
3) Industrene 120 Linseed Fatty Acid, from Witco Corporation, Humko Chemical Division, One American Lane, Greenwich, Conn. 06831
4) Emery 618 Soya Fatty Acid, from Henkel Corporation, Emery Group, 11501 Northlake Drive, Cincinnati, Ohio, 45249
5) Emersol 315 Linoleic acid, from Henkel Corporation, Emery Group, 11501 Northlake Drive, Cincinnati, Ohio, 45294
6) Linoleic Acid, 99 plus %, from Aldrich Chemical Company, Inc., 1001 West Saint Paul Avenue, Milwaukee, Wis. 53233
7) R-910 Canola Fatty Acid, from Proctor and Gamble, Chemicals Division, P.O. Box 599, Cincinnati, Ohio 45201
8) Oleic acid, 99 plus I, from Aldrich Chemical Company, Inc. 1001 West Saint Paul Avenue, Milwaukee, Wis. 53233
9) Tung oil methyl ester, from RTD Chemical Corporation, 1500 Rte. 517, Suite 305, Hackettstown, N.J. 07840
10) SAFACID UDF fish oil acids, from Pronova Oleochemicals a.s., Framnesvein 54, P.O. Box 2051, Hasle, N-3202 Sandefjord, Norway
11) SAFACID U fish oil acids, from Pronova Oleochemicals a.s.,Framnesvein 54, P.O. Box 2051, Hasle, N-3202 Sandefjord, Norway
12) Ethyl sorbate, 99%, from Fisher Scientific, Acros Organics, 711 Forbes Avenue, Pittsburgh Pa. 15219
13) 2,4-hexadienoic acid, 99% (sorbic acid), from Fisher Scientific, Acros Organics, 711 Forbes Avenue, Pittsburgh Pa. 15219
14) Trans-cinnamic acid, from Fisher Scientific, Acros Organics, 711 Forbes Avenue, Pittsburgh Pa. 15219
15) Dimethylitaconate, 97%, from Aldrich Chemical Company, Inc., 1001 West Saint Paul Avenue, Milwaukee, Wis. 53233
16) Itaconic acid, 99 plus %, from Aldrich Chemical Company, Inc., 1001 West Saint Paul Avenue, Milwaukee, Wis. 53233
17) 2-octadecen-1-ylsuccinic anhydride, from The Humphrey Chemical Company, Inc., 45 Devine Street, North Haven, Conn. 06473
18) 2-dodecen-1-ylsuccinic anhydride, 97%, from Aldrich Chemical Company, Inc., 1001 West Saint Paul Avenue, Milwaukee Wis. 53233

D. Saturated Acids
1) Stearic Acid, 90%, from Sigma Chemical Company, P.O. Box 14508, St. Louis, Mo.

E. Catalysts
1) Phosphorous Acid, from Albright & Wilson Americas, P.O. Box 26229, Richmond, Va. 23229
2) TYZOR TPT tetraisopropyl titanate, from E. I. du Pont de Nemours and Company, Wilmington Del.

EXAMPLES

Example 1

A 250-ml, 4-neck round-bottom flask, fitted with a mechanical agitator, temperature control device, Dean-Stark trap, condenser, and nitrogen inlet/outlet was charged with 56.07 g Emery 644 Linseed Fatty Acid, 75.84 g ZONYL BA Fluorotelomer Intermediate and 0.17 g aqueous 70% phosphorous acid. The mixture was heated to and held at about 145° C. for about 45 hours to yield fluorinated ester at which time the mixture contained 0.05% residual ZONYL BA by gas chromoatographic (GC) analysis and 37.9% fluorine by combustion analysis.

Example 2

A 1000-ml, 4-neck round-bottom flask, fitted with a mechanical agitator, temperature control device, Dean-Stark trap, condenser, and nitrogen inlet/outlet was charged with 420 g TRLA-50 Linseed Fatty Acid, 566 g ZONYL BA Fluorotelomer Intermediate and 0.65 g aqueous 70% phosphorous acid. The mixture was heated to and held at about 145° C. for about 24.5 hours to yield fluorinated ester at which time the mixture contained 0.18% residual ZONYL BA by GC analysis and 38.2% fluorine by combustion analysis.

Example 3

A 250-ml, 4-neck round-bottom flask, fitted with a mechanical agitator, temperature control device, Dean-Stark trap, condenser, and nitrogen inlet/outlet was charged with 56.07 g Industrene 120 Linseed Fatty Acid, 75.84 g ZONYL BA Fluorotelomer Intermediate and 0.17 g aqueous 70% phosphorous acid. The mixture was heated to and held at about 145° C. for about 25 hours to yield fluorinated ester at which time the mixture contained 0.07% residual ZONYL BA by GC analysis and 37.9% fluorine by combustion analysis.

Example 4

A 1000-ml, 4-neck round-bottom flask equipped with a mechanical agitator, temperature control device, Dean-Stark trap, condenser and nitrogen inlet/outlet was charged with 210.39 g Emery 618 Soya Fatty Acid, 302.70 g ZONYL BA Fluorotelomer Intermediate and 0.37 g aqueous 70% phosphorous acid. The mixture was heated to and held at about 145° C. for about 24 hours to yield fluorinated ester at which time the mixture contained 0.30% residual ZONYL BA by GC analysis and 37.8% fluorine by combustion analysis.

Example 5

A 250-ml, 4-neck round-bottom flask, fitted with a mechanical agitator, temperature control device, Dean-Stark trap, condenser, and nitrogen inlet/outlet was charged with 56.58 g Emersol 315 Linoleic Acid, 76.97 g ZONYL BA Fluorotelomer Intermediate and 0.13 g aqueous 70% phosphorous acid. The mixture was heated to and held at about 145° C. for about 45 hours to yield fluorinated ester at which time the mixture contained 0.09% ZONYL BA by GC analysis and 38.5% fluorine by combustion analysis.

Example 6

A 100-ml, 3-neck round-bottom flask equipped with a mechanical agitator, temperature control device, short-path distillation head, condenser, receiver and nitrogen inlet/outlet was charged with 24.96 g linoleic acid, 99 plus %, 42.26 g ZONYL BA Fluorotelomer Intermediate and 0.12 g aqueous 70% phosphorous acid. The mixture was heated to and held about 145° C. for about 45 hours at which time it contained 0.04w residual ZONYL BA by GC analysis and 42.2% fluorine by combustion analysis. Product esters having the following molecular weights were identified by gas chromatography/mass spectrometric (GC/MS) analysis as components of the reaction mixture.

| | n | | | | | | |
|---|---|---|---|---|---|---|---|
| R | 2 | 3 | 4 | 5 | 6 | 7 | 8 |
| $C_{17}H_{31}$ | | 526 | 626 | 726 | 826 | 926 | 1026 | 1126 |

R and n are as previously defined.

Example 7

A 250-ml, 4-neck round-bottom flask, fitted with a mechanical agitator, temperature control device, Dean-Stark trap, condenser, and nitrogen inlet/outlet was charged with 106.29 g R-910 Canola Fatty Acid, 144.22 g ZONYL BA Fluorotelomer Intermediate and 0.19 g aqueous 70% phosphorous acid. The mixture was heated to and held at about 145° C. for about 44 hours to yield fluorinated ester at which time the mixture contained 0.04% residual ZONYL BA by GC analysis and 38.3% fluorine by combustion analysis.

Example 8

A 100-ml, 3-neck round-bottom flask equipped with a mechanical agitator, temperature control device, short-path distillation head, condenser, receiver and nitrogen inlet/outlet was charged with 25.50 g oleic acid, 99 plus %, 42.88 g ZONYL BA Fluorotelomer Intermediate and 0.13 g aqueous 70% phosphorous acid. The mixture was heated to and held at about 145° C. for about 26 hours to yield fluorinated ester at which time the mixture contained 0.10% residual ZONYL BA by GC analysis and 41.6% fluorine by combustion analysis.

Example 9

A 250-ml, 4-neck round-bottom flask, fitted with a mechanical agitator, temperature control device, Dean-Stark trap, condenser, and nitrogen inlet/outlet was charged with 58.38 g tung oil methyl esters and 86.61 g ZONYL BA Fluorotelomer Intermediate. The mixture was heated to and held at about 150° C. for about 40 hours, with the addition of 0.4940, 0.5497, 0.4976 and 0.4735 g TYZOR TPT tetraisopropyl titanate at about zero, 2, 4 and 23 elapsed hours, respectively, at which time it contained 2.33% residual ZONYL BA by GC analysis and 41.1% fluorine by combustion analysis. Product esters having the following molecular weights were identified by GC/MS analysis as components of the reaction mixture.

| R | n=3 | 4 | 5 | 6 | 7 |
|---|---|---|---|---|---|
| $C_{15}H_{31}$* | 602 | 702 | 802 | 902 | 1002 |
| $C_{17}H_{35}$* | 630 | 730 | 830 | 930 | 1030 |
| $C_{17}H_{33}$ | 628 | 728 | 828 | 928 | 1028 |
| $C_{17}H_{31}$ | 626 | 726 | 826 | 926 | |
| $C_{17}H_{29}$ | 624 | 724 | 824 | 924 | 1024 |

R and n are as previously defined.
*In addition these saturated esters were present, derived from saturated components of the acid.

Example 10

A 250-ml, 4-neck round-bottom flask, fitted with a mechanical agitator, temperature control device, Dean-Stark trap, condenser, and nitrogen inlet/outlet was charged with 59.61 g SAFACID UDF fish oil acids (acid number 188), 76.98 g ZONYL BA Fluorotelomer Intermediate and 0.15 g aqueous 70% phosphorous acid. The mixture was heated to and held at about 145° C. for about 28 hours, at which time it contained about 0.6% residual ZONYL BA by GC analysis and 37.9% fluorine by combustion analysis. Product esters having the following molecular weights were identified by GC/MS analysis as components of the reaction mixture.

| R | n=3 | 4 | 5 | 6 | 7 | 8 |
|---|---|---|---|---|---|---|
| $C_{13}H_{27}$* | 574 | 674 | 774 | 874 | 974 | |
| $C_{15}H_{31}$* | 602 | 702 | 802 | 902 | 1002 | |
| $C_{15}H_{29}$ | 600 | 700 | 800 | 900 | | |
| $C_{17}H_{35}$* | 630 | 730 | 830 | 930 | | |
| $C_{17}H_{33}$ | 628 | 728 | 828 | 928 | 1028 | 1128 |
| $C_{17}H_{31}$ | 626 | 726 | | | | |
| $C_{19}H_{37}$ | 656 | 756 | 856 | 956 | 1056 | |
| $C_{19}H_{29}$ | 648 | 748 | 848 | 948 | 1048 | |
| $C_{21}H_{41}$ | 684 | 784 | 884 | 984 | 1084 | |
| $C_{21}H_{31}$ | 674 | 774 | 874 | 974 | 1074 | |

R and n are as previously defined.
*In addition these saturated esters were present, derived from saturated components of the acid.

Example 11

A 250-ml, 4-neck round-bottom flask, fitted with a mechanical agitator, temperature control device, Dean-Stark trap, condenser, and nitrogen inlet/outlet was charged with 62.01 g SAFACID U fish oil acids (acid number 181), 76.94 g ZONYL BA Fluorotelomer Intermediate and 0.27 g aqueous 70% phosphorous acid. The mixture was heated to and held at about 145° C. for about 25 hours, at which time it contained about 0.5% residual ZONYL BA by GC analysis and 36.6% fluorine by combustion analysis. Product esters having the following molecular weights were identified by GC/MS analysis as components of the reaction mixture.

| R | n=3 | 4 | 5 | 6 | 7 | 8 |
|---|---|---|---|---|---|---|
| $C_{11}H_{23}$* | 546 | 646 | 746 | 846 | 946 | 1046 |
| $C_{13}H_{27}$* | 574 | 674 | 774 | 874 | 974 | 1074 |
| $C_{15}H_{31}$* | 602 | 702 | 802 | 902 | 1002 | |
| $C_{15}H_{29}$ | 600 | 700 | 800 | 900 | | |
| $C_{17}H_{35}$* | 630 | 730 | 830 | 930 | | |
| $C_{17}H_{33}$ | 628 | 728 | 828 | 928 | 1028 | |
| $C_{17}H_{31}$ | 626 | 726 | 826 | | | |
| $C_{19}H_{37}$ | 656 | 756 | 856 | 956 | 1056 | |
| $C_{19}H_{29}$ | 648 | 748 | 848 | 948 | | |
| $C_{21}H_{41}$ | 684 | 784 | 884 | 984 | | |
| $C_{21}H_{31}$ | 674 | 774 | 874 | 974 | | |

R and n are as previously defined.
*In addition these saturated esters were present, derived from saturated components of the acid.

Example 12

A 250-ml, 4-neck round-bottom flask, fitted with a mechanical agitator, temperature control device, Dean-Stark trap, condenser, and nitrogen inlet/outlet was charged with 30.83 g ethyl sorbate, 99% and 94.82 g ZONYL BA Fluorotelomer Intermediate. The mixture was heated to and held at about 125° C. for about 2 hours, at which time 5 drops of TYZOR TPT tetraisopropyl titanate was added and the temperature raised to and held at about 150° C. for about 268 hours, with additional 5 drop additions of TYZOR TPT after 22 and 73 elapsed hours to yield fluorinated ester. The product mixture contained 0.58% residual ZONYL BA by GC analysis and 53.3% fluorine by combustion analysis.

Example 13

A 250-ml, 4-neck round-bottom flask, fitted with a mechanical agitator, temperature control device, Dean-Stark trap, condenser, and nitrogen inlet/outlet was charged with 28.00 g 2,4-hexadienoic acid (sorbic acid), 94.81 g ZONYL BA Fluorotelomer Intermediate and 0.31 g aqueous 70% phosphorous acid. The mixture was heated to and held at about 130° C. for about 269 hours to yield fluorinated ester at which time the mixture contained 0.27% residual ZONYL BA by GC analysis and 51.0% fluorine by combustion analysis.

Example 14

A 250-ml, 4-neck round-bottom flask, fitted with a mechanical agitator, temperature control device, Dean-Stark trap, condenser, and nitrogen inlet/outlet was charged with 31.23 g trans-cinnamic acid, 96.25 g ZONYL BA Fluorotelomer Intermediate and 0.21 g aqueous 70% phosphorous acid. The mixture was heated to and held at about 145° C. for about 156 hours to yield fluorinated ester at which time the mixture contained 0.24% residual ZONYL BA by GC analysis and 51.5% fluorine by combustion analysis. Product esters having the following molecular weights were identified by GC/MS analysis as components of the reaction mixture.

| R | n=3 | 4 | 5 | 6 | 7 | 8 | 9 | 10 |
|---|---|---|---|---|---|---|---|---|
| $C_9H_9$ | 494 | 594 | 694 | 794 | 894 | 994 | 1094 | 1194 |

R and n are as previously defined.

Example 15

A 250-ml, 4-neck round-bottom flask, fitted with a mechanical agitator, temperature control device, Dean-Stark trap, condenser, and nitrogen inlet/outlet was charged with 48.95 g dimethylitaconate, 97%, and 129.82 g ZONYL BA Fluorotelomer Intermediate. The mixture was heated to and held at about 139° C. for about 66 hours, with the addition of 1.1955, 1.2020 and 0.5595 g TYZOR TPT tetraisopropyl titanate at about zero, 18 and 44.5 elapsed hours, respectively. The reaction product mixture contained about 2.42% residual ZONYL BA by GC analysis, 50.8% fluorine by combustion analysis and product esters having the following molecular weights as identified by GC/MS analysis.

|  | n | | | | | | |
|---|---|---|---|---|---|---|---|
| R | 3 | 4 | 5 | 6 | 7 | 8 | 9 |
| $CH_3$ | 490 | 590 | 690 | 790 | 890 | 990 | 1090 |
| $C_3H_7$ | 518 | 618 | 718 | 818 | | | |

|  | n | | | |
|---|---|---|---|---|
| n* | 3 | 4 | 5 | 6 |
| 3 | 822 | 922 | 1022 | 1122 |
| 4 | | 1022 | 1122 | 1222 |
| 5 | | | 1222 | | n is as previously defined. R is an alkyl radical introduced from the catalyst or the starting ester.
*Occurs when acid groups react with distinct ZONYL BA homologues.

Example 16

A 250-ml, 4-neck round-bottom flask, fitted with a mechanical agitator, temperature control device, Dean-Stark trap, condenser, and nitrogen inlet/outlet was charged with 19.54 g itaconic acid, 99%, 144.20 g ZONYL BA Fluorotelomer Intermediate and 0.22 g aqueous 70% phosphorous acid. The mixture was heated to and held at about 145° C. for about 134 hours to yield fluorinated ester at which time the mixture contained 2.19% residual ZONYL BA by GC analysis and 62.95 fluorine by combustion analysis.

Example 17

A 250-ml, 4-neck round-bottom flask, fitted with a mechanical agitator, temperature control device, Dean-Stark trap, condenser, and nitrogen inlet/outlet was charged with 28.3 g 2-octadecen-1-ylsuccinic anhydride, 84.2 g ZONYL BA-N Fluorotelomer Intermediate, 0.2 g aqueous 70% phosphorous acid and 0.08 g boric acid. The mixture was heated to and held at about 145° C. for about 48 hours. The reaction mixture, isolated as a tan, waxy solid, m.p. 42.4° C. by differential scanning calorimetry (DSC), contained 49.2% fluorine by combustion analysis and product esters having the following molecular weights as identified by GC/MS analysis.

|  | n | | | | | |
|---|---|---|---|---|---|---|
| n | 3 | 4 | 5 | 6 | 7 | 8 |
| 3 | | 1160 | 1260 | 1360 | 1460 | |
| 4 | | 1260 | 1360 | 1460 | 1560 | 1660 |
| 5 | 1260 | 1360 | 1460 | 1560 | 1660 | |
| 6 | | 1460 | 1560 | 1660 | | |
| 7 | | 1560 | 1660 | | | | n is as previously defined.

Example 18

A 250-ml, 4-neck round-bottom flask, fitted with a mechanical agitator, temperature control device, Dean-Stark trap, condenser, and nitrogen inlet/outlet was charged with 45.22 g Emery 644 Linseed Fatty Acid, 78.16 g bis-(perfluoroalkylethylmercapto)neopentyl glycols of the formula $[F(CF_2CF_2)_nCH_2CH_2SCH_2]_2C(CH_2OH)_2$ where n is 3 to 8, predominantly 3, 4 and 5, and 0.18 g aqueous 70% phosphorous acid. The mixture was heated to and held at about 145° C. for about 42 hours to yield fluorinated ester at which time the mixture contained 0.48i residual ZONYL BA by GC analysis and 38.4% fluorine by combustion analysis.

Example 19

A 250-ml, 4-neck round-bottom flask, fitted with a mechanical agitator, temperature control device, Dean-Stark trap, condenser, and nitrogen inlet/outlet was charged with 69.56 g Emery 644 Linseed Fatty Acid, 111.43 g FX-42 and 0.15 g aqueous 70% phosphorous acid. The mixture was heated to and held at about 145° C. for about 72.5 hours to yield fluorinated ester at which time the mixture contained 0.41% residual FX-42 by GC analysis and 36.8% fluorine by combustion analysis.

Example 20

A 250-ml, 4-neck round-bottom flask, fitted with a mechanical agitator, temperature control device, Dean-Stark trap, condenser, and nitrogen inlet/outlet was charged with 26.63 g 2-dodecen-1-ylsuccinic anhydride, 116.83 g FX-42 and 0.18 g aqueous 70% phosphorous acid. The mixture was heated to and held at about 145° C. for about 48 hours to yield fluorinated ester, at which time it was free of carboxylic acid/anhydride functionality by Infrared analysis and contained 44.9% fluorine by combustion analysis.

Example 21

Synthesis of R—CO—S—X—$R_f$ wherein R is a fatty acid hydrocarbon radical, X is —$CH_2CH_2$—, and $R_f$ is a fluorocarbon radical of the formula $F(CF_2CF_2)_n{}^-$, where n is 4 to 7.

A 250-ml, 4-neck round-bottom flask, fitted with a mechanical agitator, temperature control device, Dean-Stark trap, water condenser, and nitrogen inlet/outlet was charged with 75.02 gm perfluoroalkylethyl thiols of the formula $F(CF_2CF_2)_nCH_2CH_2SH$, where n is 4 to 7, 48.76 gm Emery 644 linseed fatty acid and 0.16 gm aqueous 70% phosphorous acid. The mixture was heated to and held at about 145° C. for about 263 hours, at which time it contained about 0.130 residual fluorothiol by GC analysis, 36.1% fluorine by combustion analysis and product esters having the following molecular weights as identified by GC/MS analysis.

|  | n | | | |
|---|---|---|---|---|
| R | 4 | 5 | 6 | 7 |
| $C_{15}H_{31}$* | 718 | 828 | 918 | 1018 |
| $C_{17}H_{35}$* | 746 | 846 | 946 | 1046 |
| $C_{17}H_{33}$ | 744 | 844 | 944 | 1044 |
| $C_{17}H_{32}$ | 742 | 842 | 942 | |
| $C_{17}H_{29}$ | 740 | 840 | 940 | |

R and n are as previously defined.
*In addition these saturated thiol esters were present derived from saturated components of the acid.

Comparative Example A

A 250-ml, 4-neck round-bottom flask, fitted with a mechanical agitator, temperature control device, Dean-Stark trap, condenser, and nitrogen inlet/outlet was charged with 56.86 g stearic acid, 90%, 75.98 g ZONYL BA Fluorotelomer Intermediate, and 0.20 g aqueous 70% phosphorous acid. The mixture was heated to and held at about 145° C. for about 24 hours to yield fluorinated ester at which time the mixture contained about 0.05% residual ZONYL BA by GC analysis and 37.6% fluorine by combustion analysis.

Comparative Example B

A 250-ml, 4-neck round-bottom flask, fitted with a mechanical agitator, temperature control device, Dean-Stark trap, condenser, and nitrogen inlet/outlet was charged with 25.96 g diethylmaleate, 97%, 137.02 g ZONYL BA Fluorotelomer Intermediate and 0.22 g aqueous phosphorous acid. The mixture was heated to and held at about 145° C., with the addition of 1.4 g and 0.9 g TYZOR TPT tetraisopropyl titanate and 2.0 g diethylmaleate, 97%., after about 25, 44.5 and 51 elapsed hours, respectively, for about 70 hours to yield fluorinated ester at which time the mixture contained 6.74% residual ZONYL BA by GC analysis and 60.3% fluorine by combustion analysis. Maleic and fumaric acid esters having the following molecular weights were identified by GC/MS analysis as components of the product mixture.

|   | n | | | |
|---|---|---|---|---|
|   | 3 | 4 | 5 | 6 |
| R |   |   |   |   |
| $C_2H_5$ | 490 | 590 | 690 | 790 |
| $C_3H_7$ | 504 | 604 | 704 | 804 |
| n |   |   |   |   |
| 3 | 808 | 908 | 1008 | 1108 |
| 4 | 908 | 1008 | 1108 | 1208 |
| 5 | 1008 | 1108 | 1208 | 1308 | n is as previously defined. R is an alkyl radical introduced from the catalyst or the starting ester.

Example 22

The esters of examples 1 to 21 and comparative examples A and B were mixed into the coating compositions as indicated in Tables 3–8 in an amount to give a 1000 μg/g fluorine concentration in the blended product and the resultant ester-containing coating composition cast on a Leneta P-121-10N dull black, scrub test panel. The coating was evaluated after drying by Test Method 1 to measure the advancing (Adv) and receding (Rec) contact angles, tested for wash durability by Test Method 2, and for anti-blocking properties by Test Method 3 as described above.

TABLE 3

Test Results on IMPERVO White Alkyd High Gloss Enamel

| Ex. No. | Test Method 1 Dried Coating | | | | Test Method 2 Wash Durability | | Test Method 3 Anti-blocking Cure Day | | | |
|---|---|---|---|---|---|---|---|---|---|---|
|   | Water | | Hexadecane | | Hexadecane | | | | | |
|   | Adv | Rec | Adv | Rec | Adv | Rec | 1 | 2 | 3 | 4 |
| control | 83 | 42 | 18 | 0 | 15 | 0 | 0 | 3 |   | 7 |
| 1 | 124 | 87 | 81 | 63 | 70 | 38 |   |   |   |   |
| 2 | 124 | 99 | 81 | 65 | 70 | 40 |   |   |   |   |
| 3 | 127 | 89 | 82 | 59 | 72 | 52 | 8 | 9 |   | 10 |
| 4 | 125 | 85 | 82 | 51 | 70 | 42 |   |   |   |   |
| 5 | 123 | 88 | 81 | 69 | 70 | 40 | 9 | 10 |   |   |
| 6 | 124 | 96 | 82 | 75 | 71 | 49 |   |   |   |   |

TABLE 3-continued

Test Results on IMPERVO White Alkyd High Gloss Enamel

| Ex. No. | Test Method 1 Dried Coating | | | | Test Method 2 Wash Durability | | Test Method 3 Anti-blocking Cure Day | | | |
|---|---|---|---|---|---|---|---|---|---|---|
|   | Water | | Hexadecane | | Hexadecane | | | | | |
|   | Adv | Rec | Adv | Rec | Adv | Rec | 1 | 2 | 3 | 4 |
| 7 | 124 | 86 | 83 | 39 | 74 | 46 | 9 | 10 |   |   |
| 8 | 124 | 81 | 83 | 47 | 66 | 37 |   |   |   |   |
| 9 | 124 | 91 | 81 | 72 | 74 | 55 | 8 | 10 |   |   |
| 10 | 127 | 92 | 82 | 34 | 71 | 29 |   |   |   |   |
| 11 | 126 | 89 | 81 | 19 | 69 | 16 |   |   |   |   |
| 12 | 125 | 94 | 82 | 78 | 74 | 49 |   |   |   |   |
| 13 | 15 | 90 | 82 | 78 | 74 | 49 | 8 | 9 |   | 10 |
| 14 | 124 | 85 | 81 | 49 | 72 | 48 | 9 | 10 |   |   |
| 15 | 125 | 84 | 84 | 66 | 80 | 60 | 9 | 9 |   | 10 |
| 16 | 122 | 83 | 83 | 68 | 81 | 57 |   |   |   |   |
| 17 | 118 | 81 | 81 | 34 | 61 | 37 |   |   |   |   |
| 18 | 124 | 86 | 81 | 78 | 75 | 54 | 9 | 10 |   |   |
| 19 | 115 | 62 | 79 | 69 | 53 | 20 |   |   |   |   |
| 20 | 118 | 99 | 79 | 73 | 67 | 36 | 8 | 9 |   | 9 |
| 21 | 124 | 85 | 80 | 68 | 66 | 39 |   |   |   |   |
| Comparative Examples: | | | | | | | | | | |
| A | 130 | 82 | 43 | 0 | 16 | 0 |   |   |   |   |
| B | 108 | 79 | 82 | 57 | 52 | 6 |   |   |   |   |

TABLE 4

Test Results on Enterprise Gloss Polyurethane

| Example No. | Test Method 1 Contact Angles | | | |
|---|---|---|---|---|
|   | Water | | Hexadecane | |
|   | Adv | Rec | Adv | Rec |
| control | 9 | 56 | 11 | 0 |
| 4 | 123 | 94 | 8 | 61 |

TABLE 5

Test Results on Duron Exterior Alkyl House Paint

| Example No. | Test Method 1 Contact Angles | | | |
|---|---|---|---|---|
|   | Water | | Hexadecane | |
|   | Adv | Rec | Adv | Rec |
| control | 98 | 53 | 12 | 8 |
| 1 | 125 | 84 | 82 | 39 |

TABLE 6

Test Results on SWP Exterior Gloss Oil Base paint

| Example No. | Test Method 1 Contact Angles | | | |
|---|---|---|---|---|
|   | Water | | Hexadecane | |
|   | Adv | Rec | Adv | Rec |
| control | 83 | 28 | 37 | 0 |
| 1 | 124 | 91 | 82 | 49 |

TABLE 7

Test Results on 75 Neutral Gel Coat

| | Test Method 1 Contact Angles | | | |
|---|---|---|---|---|
| Example | Water | | Hexadecane | |
| No. | Adv | Rec | Adv | Rec |
| Control | 61 | 25 | 0 | 0 |
| 14 | 66 | 28 | 75 | 42 |
| 16 | 90 | 47 | 83 | 64 |
| Comparative Example: | | | | |
| B | 72 | 32 | 72 | 0 |

TABLE 8

Test Results on Neste Gel Coat WG30001S

| | Test Method 1 Contact Angles | | | |
|---|---|---|---|---|
| Example | Water | | Hexadecane | |
| No. | Adv | Rec | Adv | Rec |
| control | 73 | 49 | 0 | 0 |
| 1 | 95 | 51 | 69 | 24 |
| 18 | 112 | 48 | 76 | 54 |

What is claimed is:

1. A coating composition comprising
  A. an ester of an unsaturated acid and a fluorinated alcohol or thiol selected from the group consisting of the Formula 1a, 1b and 2, $R_f$—X—S—OC—R,  Formula 1a
  $R_f$—X—A—OC—$R_x$—CO—A—X—$R_f$,  Formula 1b $$R-CO {\left[ \begin{array}{c} R_f-X-A-CH_2 \\ | \\ O-CH_2-C-CH_2 \\ | \\ R_f-X-A-CH_2 \end{array} \right]}_a O-OC-R \quad \text{Formula 2}$$

wherein:
  $R_f$ is a $C_2$–$C_{20}$ perfluoroalkyl radical, or a $C_5$–$C_{38}$ perfluoroalkyl radical having at least one ether oxygen atom;
  R is a $C_3$–$C_{21}$ unsaturated aliphatic hydrocarbon radical, a $C_8$–$C_{13}$ aryl radical having at least one non-aromatic double bond, or mixtures thereof;
  X is independently —$(CH2)_m$-, —$CON(R_1)R_2$—, —$SO_2N(R_1)R_2$- or —$(OCH_2CHR_3)_b O$-, wherein m is 1 to about 20; b is 3 to about 15;
  $R_1$ is H or alkyl radical of 1 to about 4 carbon atoms, $R_2$ is $C_1$–$C_{12}$ alkylene, and $R_3$ is H or $CH_2Cl$;
  A is O or S;
  $R_x$ is a divalent $C_3$–$C_{22}$ unsaturated aliphatic hydrocarbon radical; a divalent $C_8$–$C_{13}$ aryl radical having at least one non-aromatic double bond, or mixtures thereof;
  a is 1 or 2;
  and
  B. an alkyd, Type I urethane or unsaturated polyester resin; wherein a cured coating resulting from said coating composition has an advancing hexadecane contact angle of at least about 40 degrees has durable oil and water repellancy.

2. The composition of claim 1 wherein $R_f$ is selected from the group consisting of
  (a) $F(CF_2)_n$— wherein n is 2 to about 20;
  (b)

$$CF_3-CF-O-(CF_2CF_2)_e- \\ | \\ CF_3$$

wherein e is 1 to about 5; and
  (c)

$$F(CF_2)_g-O {\left( \begin{array}{c} CF-CF_2-O \\ | \\ CF_3 \end{array} \right)}_h CF- \\ | \\ CF^3$$

wherein g is 1 to about 6, and h is about 3 to about 10.

3. The composition of claim 1 wherein $R_f$ is $F(CF_2)_n$— wherein n is 2 to about 20.

4. The composition of claim 3 wherein R is a $C_{15}$ to $C_{18}$ unsaturated alkenyl group having at least one double bond.

5. The composition of claim 1 having an advancing hexadecane contact angle of at least 60 degrees.

6. The composition of claim 1 having from about 50 to about 10,000 μg/g by weight of fluorine based on nonvolatile content of the coating composition.

7. A cured coating composition comprising:
  A. an ester of an unsaturated acid and a fluorinated alcohol or thiol selected from the group consisting of the Formula 1a, 1b, and 2

$R_f$—X—S—OC—R,  Formula 1a
  $R_f$—X—A—OC—$R_x$—CO—A—X—$R_f$,  Formula 1b $$R-CO {\left[ \begin{array}{c} R_f-X-A-CH_2 \\ | \\ O-CH_2-C-CH_2 \\ | \\ R_f-X-A-CH_2 \end{array} \right]}_a O-OC-R \quad \text{Formula 2}$$

wherein:
  $R_f$ is a $C_2$–$C_{20}$ perfluoroalkyl radical, or a C5–$C_{38}$ perfluoroalkyl radical having at least one ether oxygen atom;
  R is a $C_3$–$C_{21}$ unsaturated aliphatic hydrocarbon radical, a $C_8$–$C_{13}$ aryl radical having at least one non-aromatic double bond, or mixtures thereof;
  X is independently —$(CH_2)_m^-$, —$CON(R_1)R_2$—, —$SO_2N(R_1)R_2$- or —$(OCH_2CHR_3)_b O$-, wherein m is 1 to about 20; b is 3 to about 15;
  $R_1$ is H or alkyl radical of 1 to about 4 carbon atoms, $R_2$ is $C_1$–$C_{12}$ alkylene, and $R_3$ is H or $CH_2Cl$;
  A is O or S;
  $R_x$ is a divalent $C_3$–$C_{22}$ unsaturated aliphatic hydrocarbon radical; a divalent $C_8$–$C_{13}$ aryl radical having at least one non-aromatic double bond, or mixtures thereof;
  a is 1 or 2,
  and
  B. an alkyd, urethane or unsaturated polyester resin; wherein a cured coating resulting from said coating composition has an advancing hexadecane contact angle of at least about 40 degrees.

8. A method of improving the oil repellency of an alkyd, urethane or unsaturated polyester coating composition comprising adding to said coating composition an effective amount of an ester of an unsaturated acid and a fluorinated alcohol or thiol selected from the group consisting of the Formula 1a, 1b, and 2

$$R_f\text{—}X\text{—}S\text{—}OC\text{—}R, \quad \text{Formula 1a}$$

$$R_f\text{—}X\text{—}A\text{—}OC\text{—}R_x\text{—}CO\text{—}A\text{—}X\text{—}R_f, \quad \text{Formula 1b}$$

$$R\text{—}CO\!\left[\!\begin{array}{c} R_f\text{—}X\text{—}A\text{—}CH_2 \\ | \\ O\text{—}CH_2\text{—}C\text{—}CH_2 \\ | \\ R_f\text{—}X\text{—}A\text{—}CH_2 \end{array}\!\right]_{\!a}\!\!\!O\text{—}OC\text{—}R \quad \text{Formula 2}$$

wherein:

$R_f$ is a $C_2$–$C_{20}$ perfluoroalkyl radical, or a $C_5$–$C_{38}$ perfluoroalkyl radical having at least one ether oxygen atom;

R is a $C_3$–$C_{21}$ unsaturated aliphatic hydrocarbon radical, a $C_8$–$C_{13}$ aryl radical having at least one non-aromatic double bond, or mixtures thereof;

X is independently —$(CH_2)_m$—, —$CONR_1R_2$—, —$SO_2NR_1R_2$— or —$(OCH_2CHR_3)_bO$-, wherein m is 1 to about 20; b is 3 to about 15;

$R_1$ is H or alkyl radical of 1 to about 4 carbon atoms, $R_2$ is $C_1$–$C_{12}$ alkylene, and $R_3$ is H or $CH_2Cl$;

A is O or S;

$R_x$ is a divalent $C_3$–$C_{22}$ unsaturated aliphatic hydrocarbon radical; a divalent $C_8$–$C_{13}$ aryl radical having at least one non-aromatic double bond, or mixtures thereof; and a is 1 or 2.

* * * * *